United States Patent [19]
Sullivan et al.

[11] Patent Number: 5,616,490
[45] Date of Patent: Apr. 1, 1997

[54] RIBOZYMES TARGETED TO TNF-α RNA

[75] Inventors: Sean M. Sullivan; Kenneth G. Draper, both of Boulder, Colo.

[73] Assignee: Ribozyme Pharmaceuticals, Inc., Boulder, Colo.

[21] Appl. No.: 434,503

[22] Filed: May 4, 1995

Related U.S. Application Data

[63] Continuation of Ser. No. 8,895, Jan. 19, 1993, abandoned, which is a continuation-in-part of Ser. No. 989,849, Dec. 7, 1992, abandoned.

[51] Int. Cl.$^6$ ............... C07H 21/04; A61K 48/00; C12N 15/85
[52] U.S. Cl. ............... 435/366; 435/6; 435/91.31; 435/172.1; 435/172.3; 435/320.1; 435/325; 435/364; 435/367; 536/23.1; 536/23.2; 536/24.5; 514/44
[58] Field of Search ............... 435/6, 91.31, 172.1, 435/172.3, 320.1, 240.1, 240.2; 536/23.1, 23.2, 24.5; 514/44

[56] References Cited

U.S. PATENT DOCUMENTS

| | | | |
|---|---|---|---|
| 4,987,071 | 1/1991 | Cech | 435/91.31 |
| 5,168,053 | 8/1990 | Altman et al. | 514/44 |

FOREIGN PATENT DOCUMENTS

| | | |
|---|---|---|
| 9115580 | 10/1991 | WIPO . |
| 9118625 | 12/1991 | WIPO . |
| 9118913 | 12/1991 | WIPO . |
| 9118624 | 12/1991 | WIPO . |
| 9200080 | 1/1992 | WIPO . |

OTHER PUBLICATIONS

Baringa, "Ribozymes: Killing the Messenger," *Science* 262:1521–1514 (1993).
Cech, "Ribozymes and Their Medical Implications" *JAMA* 260:3030–3034 (1988).
Guerrier-Takada et al., "The RNA Moiety of Ribonuclease P Is the Catalytic Subunit of the Enzyme," *Cell* 35:849–857 (1983).
Hampel and Tritz, "RNA Catalytic Properties of the Minimum (−)sTRSV Sequence," *Biochemistry* 28:4929–4933 (1989).
Hampel et al., "'Hairpin' Catalytic RNA Model: Evidence for Helices and Sequence Requirement for Substrate RNA", *Nucleic Acids Research* 18:299–304 (1990).
Hampel et al., *Nucleic Acids Research* 18:299 (1990).
Haseloff and Gerlach, "Simple RNA Enzymes with New and Highly Specific Endoribonuclease Activities," *Nature* 334:585–591 (1988).
Hession et al., WO 9013300 (Nov. 15, 1990) provided as CA Abstr. Acc# 114(25): 292037g.
Johnston and Hoth, "Present Status and Future Prospects for HIV Therapies," *Science* 260:1286–1293 (1993).
Kim et al., *Proc. Natl. Acad. Sci. USA* 84:788 (1987).
Mamone et al., "Design of Hammerhead Ribozymes Targeted to Sequences in HIV, HSV and the RAT ANF Gene," Abstract of Keystone, CO (May 27, 1992).
Pavco et al., "Regulation of Self–Splicing Reactions by Antisense RNA," Abstract of Keystone, CO (May 27, 1992).
Perrotta and Been, "Cleavage of Oligoribonucleotides by a Ribozyme Derived from the Hepatitis δ Virus RNA Sequence," *Biochemistry* 31:16–21 (1992).
Rossi et al, "Ribozymes as Anti–HIV–1 Therapeutic Agents: Principles, Applications, and Problems," *Aids Research and Human Retroviruses* 8:183 (1992).
Rossi et al., "Ribozyme Mediated Intracellular Immunity to HIV–1 in CD4," *J. Cell Biochem.* Suppl 14A:D428 (1990).
Sarver et al., "Ribozymes as Potential Anti–HIV–1 Therapeutic Agents" *Science* 247:1222–1225 (1990).
Sioud et al., *J. Mol. Biol.* 223:831–835 (1992).
Tanabe et al., *J. Biol. Chem.* 262:16580 (1987), provided as BIOSIS Abstr. 85047487.
Weerasinghe et al., "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme," *Journal of Virology* 65:5531–4 (1994).

*Primary Examiner*—John L. LeGuyader
*Attorney, Agent, or Firm*—Lyon & Lyon

[57] ABSTRACT

An enzymatic RNA molecule which cleaves mRNA associated with development or maintenance of an inflammatory disease.

8 Claims, 1 Drawing Sheet

RIBOZYMES TARGETED TO TNF-α RNA

This is a continuation of U.S. patent application Ser. No. 08/008,895, filed Jan. 19, 1993, now abandoned, which is a continuation-in-part of Sullivan and Draper, "Method and Reagent for Treatment of Inflammatory Disease", U.S. patent application Ser. No. 07/989,849, filed Dec. 7, 1992, now abandoned hereby incorporated by reference herein.

BACKGROUND OF THE INVENTION

This invention relates to methods for inhibition of inflammatory disease, in particular the inhibition of genetic expression which leads to the reduction or elimination of immune cell proliferation in inflammation or pre-inflammatory conditions.

Inflammation is a tissue reaction to irritation, infection or injury marked by localized heat, swelling, redness, pain and sometimes loss of function. When tissues sustain physiological injury, the afflicted cells synthesize and/or release chemicals (cytokines and cellular adhesion molecules) which attract lymphoid cells and accelerate cell growth which is required for healing. The infiltration of lymphoid cells to the wound leads to the release of more biological response modifying molecules, which include vasoregulatory substances such as bradykinin and immunoregulatory molecules exemplified by the interleukin family of proteins. As healing occurs, the immune cell infiltration wanes and the inflammatory process ceases. Under certain physiological conditions, such as those observed in psoriasis, asthma, head injuries and systemic inflammatory response syndrome (SIRS), the condition persists because of inappropriate cellular controls. A persistent inflammatory condition may be acute or chronic and is generically referred to as inflammatory disease.

Inflammatory disease is exemplified by psoriasis, which is a skin disease caused by excessive growth of basal keratinocytes in the epidermis. It is believed that this uncontrolled growth of the keratinocytes results from stimulation by infiltrating T-cells. The conversion of normal skin to a psoriatic lesion is initiated by injury to the tissue and subsequent recognition of the injury by circulating immune cells. An acute inflammatory reaction ensues and results in the release of various cytokines and growth factors, including tumor necrosis factor alpha (TNF-α) and interleukin-1 (IL-1). A number of the cytokines released by infiltrating leukocytes induce production of cell adhesion molecules on the surface of the keratinocytes, while others induce the proliferation of basal keratinocytes and result in the release of keratinocyte factors which either auto-stimulate further growth or inhibit normal controls which limit keratinocyte proliferation. The injury further results in the local activation of T-cells which return to the circulation and may cause subsequent psoriatic conditions which are quite distant from the original site of injury.

Induction of the acute phase inflammatory reactants results in the production of IL-1 and TNF-alpha; both of these molecules induce the appearance of the T-cell homing proteins, I-CAM, ELAM-1 and VCAM-1 on the cell surface of keratinocytes. TNF-α also induces the production of TGF-α, IL-6 and IL-8 by the keratinocytes. The cytokines and growth factors produced by the keratinocytes and infiltrating leukocytes cause uncontrolled keratinocyte proliferation. As the basal layer keratinocytes proliferate, the suprabasal keratinocytes are pushed closer to the surface of the skin where they normally form the cornified envelope layer and the stratum corneum. The abnormal rate of proliferation by the basal keratinocytes results in improper formation of the epidermis and stratum corneum and the ultimate development of the red, scaly appearance which is characteristic of psoriatic skin. The lack of keratinocyte growth regulation has been attributed to an unidentified mutation in a single gene or group of genes in which the keratinocytes no longer respond to the termination signal for wound healing.

There are 3 million patients in the United States afflicted with psoriasis. The available treatments for psoriasis are corticosteroids. The most widely prescribed are TEMOVATE (clobetasol propionate), LIDEX (fluocinonide), DIPROLENE (betamethasone propionate), PSORCON (diflorasone diacetate) and TRIAMCINOLONE formulated for topical application. The mechanism of action of corticosteroids is multifactorial and probably not due to simple inhibition of cell replication. This is a palliative therapy because the underlying cause of the disease remains, and upon discontinuation of the treatment the disease returns. Discontinuation of treatment is often prompted by the appearance of adverse effects such as atrophy, telangiectasias and purpura. Corticosteroids are not recommended for prolonged treatments or when treatment of large and/or inflamed areas is required. Alternative treatments include retinoids, such as etretinate, which has been approved for treatment of severe, refractory psoriasis. Alternative retinoid-based treatments are in advanced clinical trials. Retinoids act by converting keratinocytes to a differentiated state and restoration of normal skin development. Immunosuppressive drugs such as cyclosporine are also in the advanced stages of clinical trials. Due to the nonspecific mechanism of action of corticosteroids, retinoids and immunosuppressives, all current treatments of psoriasis exhibit severe side effects and should not be used for extended periods of time unless the condition is life-threatening or disabling. There is a need for a less toxic, effective therapeutic agent in psoriatic patients.

Asthma affects nearly 5% of the population in industrialized nations, yet it is underdiagnosed and undertreated. There is evidence that the incidence and prevalence of asthma are rising. These trends are occurring despite increases in the available therapies for asthma, which suggests that current methods of treating asthma are inadequate or not being utilized appropriately. Recently, it has been recognized that chronic asthma involves a characteristic inflammatory response in the airways.

Although it has long been acknowledged that fatal asthma is associated with inflammatory changes in the submucosal surfaces of the airways, it is now apparent that inflammation is present in patients with very mild asthma. Biopsies of patients have shown that infiltration of immune cells, especially eosinophils and lymphocytes, and epithelial shedding are prominent features. Further, there is a strong correlation between the degree of eosinophilia and the degree of bronchial hyperresponsiveness. Eosinophils are localized to areas of epithelial damage in the airways of patients. The basic proteins released by the eosinophils may be responsible for the damage observed in these patients. The role of mast cells and neutrophils in the disease is uncertain. Lymphocytes are present at the sites of tissue damage, but their role may be as mediators to amplify the eosinophilic response. In fact, interleukin-5, which is released by T-lymphocytes, is important in retaining and priming eosinophil action in the airway.

SUMMARY OF THE INVENTION

The invention features use of ribozymes to treat or prevent psoriasis, e.g., by inhibiting the synthesis of tumor necrosis factor in activated lymphocytes, and basal keratinocytes. The invention also features use of ribozymes to treat chronic asthma, e.g., by inhibiting the synthesis of IL-5 in lymphocytes and preventing the recruitment and activation of eosinophils. Cleavage of targeted mRNAs (tumor necrosis factor and IL-5 mRNAs) expressed in keratinocytes, T-lymphocytes, monocytes or macrophages inhibits the synthesis of tumor necrosis factor and IL-5, respectively.

A number of other cytokines may also be involved in the activation of inflammation in asthmatic patients, including platelet activating factor, IL-1, IL-3, IL-4, GM-CSF, TNFα, gamma interferon, ILAM-1, ELAM-1 and EoCSF. In addition to these cytokines, it is appreciated that any cellular receptors which mediate the activities of the cytokines are also good targets for intervention in inflammatory diseases. These targets include, but are not limited to, the IL-1R and TNFαR on keratinocytes, epithelial and endothelial cells in airways. Recent data suggest that certain neuropeptides may play a role in asthmatic symptoms. These peptides include substance P, neurokinin A and calcitonin-gene-related peptides. These target genes may have more general roles in inflammatory diseases, but are currently assumed to have a role only in asthma. Other genes which are considered to play a role in asthma are the c-myb and c-myc genes, which may be triggered to induce endothelial cell proliferation and contribute to blockage of the airways. Those skilled in the art will recognize the other potential targets noted above are also suitable for treatment with ribozymes, which will reduce the risk or occurrence of inflammatory disease, such as the interleukins (1, 3, 4, 6, and 8), glycerol transferase, selectins (E-selectin, MEL-14), cell adhesion molecules (ICAM-1, ELAM-1, VCAM-1, GMP-140, MAM), TGF-α, IL-1R, TGFαR, EoCSF, α-, β- or γ-interferon, EoCSF, GM-CSF and protein kinase C (PKC).

In particularly preferred embodiments, a ribozyme to TNFα nucleotides 374 to 393 can be use to inhibit TNFα protein production. This region may not a very good region to target because of secondary RNA structure in this region. An adjoining region which begins at nucleotide 380 in the previous reference and extends to nucleotide 412 (408–440, our sequence numbers see below) appears to contain a relatively more accessible RNA structure, and therefore represents an improved target over the region between nucleotides 374–393 (402–421, our sequence numbers).

Ribozymes are RNA molecules having an enzymatic activity which is able to repeatedly cleave other separate RNA molecules in a nucleotide base sequence specific manner. It is alleged that such enzymatic RNA molecules can be targeted to virtually any RNA transcript and efficient cleavage has been achieved in vitro. Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

This class of chemicals exhibits a high degree of specificity for cleavage of the intended target mRNA. Consequently, the ribozyme agent will only affect cells expressing that particular gene, and will not be toxic to normal tissues.

The invention can be used to treat or prevent (prophylactically) psoriasis, asthma and other inflammatory diseases. The preferred administration protocol is in vivo administration to reduce the level of TNF-α or IL-5 activity.

Thus, in the first aspect, the invention features an enzymatic RNA molecule (or ribozyme) which cleaves mRNA associated with development or maintenance of a psoriatic or asthmatic condition, e.g., mRNA encoding TNF-α, IL-5, IL-1, IL-3, IL-4, IL-6, IL-8, glycerol transferase, selectins, E-selectin, MEL-14, ICAM-1, ELAM-1, VCAM-1, GMP-140, MAM, TGFα, TNFαR, IL-1R, α-, β- or γ-interferon, GM-CSF and protein kinase C, and in particular, those mRNA targets disclosed in Table 1.

TABLE 1

| TNF-α mRNA Nucleotide Number | Sequence | SEQ. ID. NO. |
| --- | --- | --- |
| 27 | CAGCAGAGGACCAGCUA | ID. NO. 01 |
| 56 | GCAACUACAGACCC | ID. NO. 02 |
| 70 | CCCCUGAAAACAACCCUCAGACGC | ID. NO. 03 |
| 94 | CACAUCCCCUGACAAGCUGCCAGGCAGG | ID. NO. 04 |
| 134 | CACAUACUGACCCA | ID. NO. 05 |
| 157 | CCUCUCUCCCCUGGAAAGG | ID. NO. 06 |
| 176 | ACACCAUGAGCACUGAAAGCAUGAUCCGGGAC | ID. NO. 07 |
| 253 | GCCCCAGGGCUCCAGGC | ID. NO. 08 |

TABLE 1-continued

| | Sequence | SEQ. ID. NO. |
|---|---|---|
| 270 | GGUGCUUGUUCCUCAGCCUCUUC | ID. NO. 09 |
| 311 | CCACCACGCUCUUC | ID. NO. 10 |
| 362 | AAGAGUUCCCCAG | ID. NO. 11 |
| 408 | AGUCAGAUCAUCUUCUCGAACCCCGAGUGACAA | ID. NO. 12 |
| 446 | UAGCCCAUGUUGUAGCAAACCCUCAAGCUGAGGG | ID. NO. 13 |
| 574 | UACCUCAUCUACUCC | ID. NO. 14 |
| 599 | UCAAGGGCCAAGGCUGCCCCUC | ID. NO. 15 |
| 621 | CACCCAUGUGCUCCUCACCCA | ID. NO. 16 |
| 652 | CGCAUCGCCGUCUCCUACCAGACCAA | ID. NO. 17 |
| 694 | GCCAUCAAGAG | ID. NO. 18 |
| 824 | CCGACUAUCUCGACUUUGCC | ID. NO. 19 |
| 869 | UCAUUGCCCUGUGAGGAGGACGAACAUCCAACCU | ID. NO. 20 |
| 991 | CUUAGGGUCGGAACCCAA | ID. NO. 21 |
| 1043 | AAACCUGGGAUUCAGGAA | ID. NO. 22 |
| 1084 | CUGGCAACCACUAAGAAU | ID. NO. 23 |
| 1115 | UCCAGAACUCACUGG | ID. NO. 24 |
| 1187 | UGGCCAGAAUGCUGCAGGACUUGAGA | ID. NO. 25 |
| 1213 | AGACCUCACCUAGAAAUUGACACAAGU | ID. NO. 26 |
| 1276 | CUUCCUUGAGA | ID. NO. 27 |
| 1322 | UCUAUUUAUGUUUGCACUUGUG | ID. NO. 28 |
| 1344 | AUUAUUUAUUAUUUAUUUAUUAUUUAUUUAUUUA | ID. NO. 29 |
| 1378 | CAGAUGAAUGUAUUUAUUU | ID. NO. 30 |
| 1402 | ACCGGGGUAUCC | ID. NO. 31 |
| 1419 | GACCCAAUGUAGGAGCUGCCUUGGCUCAG | ID. NO. 32 |
| 1495 | AGCCCCCUGGC | ID. NO. 33 |
| 1513 | CCUUCUUUUGAUUAUGUUUUUUAAAAUAUUUAUC | ID. NO. 34 |
| 1557 | GUCUAAACAAUGCU | ID. NO. 35 |
| 1587 | GUCACUCAUUGCUGAG | ID. NO. 36 |
| 1639 | CUACUAUUCAGU | ID. NO. 37 |
| 1656 | GAAAUAAAGUUUGCUU | ID. NO. 38 |
| IL-5 mRNA Nucleotide Number | | |
| 10 | CUUUGCCAAAGGCAAAC | ID. NO. 39 |
| 33 | CGUUUCAGAGCCAUGAGGAUGC | ID. NO. 40 |
| 61 | AUUUGAGUUUGCUAGCUCUUGGAGCUG | ID. NO. 41 |
| 88 | CCUACGUGUAUGCCAUCC | ID. NO. 42 |
| 139 | AGACCUUGGCACUG | ID. NO. 43 |
| 158 | UACUCAUCGAACUCUGCUGAUA | ID. NO. 44 |
| 209 | UGUACAUAAAAA | ID. NO. 45 |
| 275 | AAACUGUGCAA | ID. NO. 46 |
| 299 | AAAGACUAUUCAAAAACUUGCC | ID. NO. 47 |
| 370 | AGACGGAGAGUAAACCAAUUCCUAGACUACCUGC | ID. NO. 48 |
| 522 | AAGAAAGAGUCA | ID. NO. 49 |
| 558 | ACUUCAGAGGGAAAG | ID. NO. 50 |
| 578 | AUUUCAGGCAUACUGACACUUUGCCAGAAAGCA | ID. NO. 51 |
| 635 | AUAUCAGAAUCA | ID. NO. 52 |
| 667 | CAAAAUUGAUAUACUUUUUUCUUAUUUAA | ID. NO. 53 |
| 738 | GAAAUGGUUAAGAAUUUG | ID. NO. 54 |

By "enzymatic RNA molecule" it is meant an RNA molecule which has complementarity in a substrate binding region to a specified mRNA target, and also has an enzymatic activity which is active to specifically cleave that mRNA. That is, the enzymatic RNA molecule is able to intermolecularly cleave mRNA and thereby inactivate a target mRNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. For in vivo treatment, complementarity between 30 and 45 bases is preferred.

In preferred embodiments, the enzymatic RNA molecule is formed in a hammerhead motif, but may also be formed in the motif of a hairpin, hepatitis delta virus, group I intron or RNAseP-like RNA (in association with an RNA guide sequence). Examples of such hammerhead motifs are described by Rossi et al., 8 *Aids Research and Humnan Retroviruses* 183, 1992, of hairpin motifs by Hampel et al., "RNA Catalyst for Cleaving Specific RNA Sequences", filed Sep. 20, 1989, which is a continuation-in-part of U.S. patent application Ser. No. 07/247,100, filed Sep. 20, 1988; Hampel and Tritz, 28 *Biochemistry* 4929, 1989; and Hampel et al., 18 *Nucleic Acids Research* 299, 1990, and an example of the hepatitis delta virus motif is described by Perrotta and Been, 31 *Biochemistry* 16, 1992, of the RNAseP motif by Guerrier-Takada et al., 35 *Cell* 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

In a second related aspect, the invention features a mammalian cell which includes an enzymatic RNA molecule as described above. Preferably, the mammalian cell is a human cell.

In a third related aspect, the invention features an expression vector which includes nucleic acid encoding an enzymatic RNA molecule described above, located in the vector, e.g., in a manner which allows expression of that enzymatic RNA molecule within a mammalian cell.

In a fourth related aspect, the invention features a method for treatment of a psoriatic or asthmatic condition by administering to a patient an enzymatic RNA molecule as described above.

The invention provides a class of chemical cleaving agents which exhibit a high degree of specificity for the mRNA causative of a psoriatic condition. Such enzymatic RNA molecules can be delivered exogenously or endogenously to infected cells. In the preferred hammerhead motif the small size (less than 40 nucleotides, preferably between 32 and 36 nucleotides in length) of the molecule allows the cost of treatment to be reduced.

The smallest ribozyme delivered for any type of treatment reported to date (by Rossi et al., 1992, supra) is an in vitro transcript having a length of 142 nucleotides. Synthesis of ribozymes greater than 109 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, an alternative approach uses smaller ribozyme motifs (e.g., of the hammerhead structure, shown generally in FIG. 1) and exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure, as well as complementary binding of the ribozyme to the mRNA target.

The enzymatic RNA molecules of this invention can be used to treat psoriatic or pre-psoriatic, asthmatic or pre-asthmatic conditions. Such treatment can also be extended to other related genes in nonhuman primates. Affected animals can be treated at the time of psoriatic or asthmatic risk detection, or in a prophylactic manner. This timing of treatment will reduce the chance of further psoriatic or asthmatic damage.

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies multiple ribozymes targeted to different genes, ribozymes coupled with known small molecule inhibitors, or intermittent treatment with combinations of ribozymes and/or other chemical or biological molecules).

Other features and advantages of the invention will be apparent from the following description of the preferred embodiments thereof, and from the claims.

DESCRIPTION OF THE PREFERRED EMBODIMENTS

Figure 1:
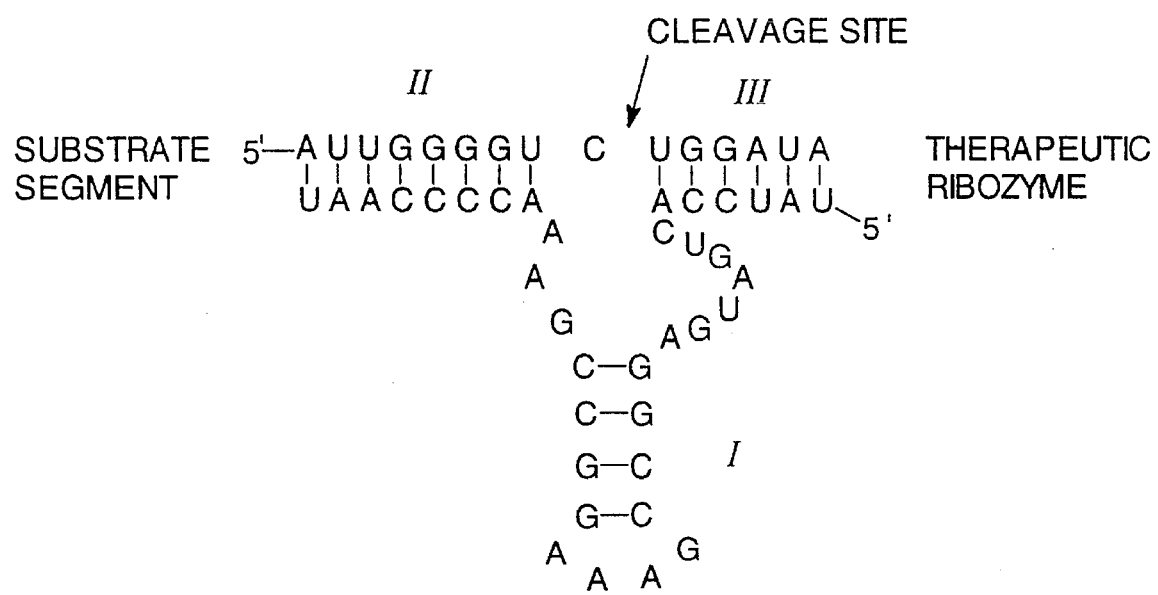

The drawing will first briefly be described.

Drawing

FIG. 1 is a diagrammatic representation of a hammerhead motif ribozyme showing stems I, II and III (marked (I), (II) and (III) respectively) interacting with a target region. The 5' and 3' ends of both ribozyme and target are shown. Dashes indicate base-paired nucleotides.

Target Sites

Ribozymes targeting selected regions of mRNA associated with inflammatory disease are chosen to cleave the target RNA in a manner which preferably inhibits translation of the RNA. Genes are selected such that inhibition of translation will preferably inhibit cell replication, e.g., by inhibiting production of a necessary protein. Selection of effective target sites within these critical regions of mRNA entails testing the accessibility of the target RNA to hybridization with various oligonucleotide probes. These studies can be performed using RNA probes and assaying accessibility by cleaving the hybrid molecule with RNAseH (see below). Alternatively, such a study can use ribozyme probes designed from secondary structure predictions of the mRNAs, and assaying cleavage products by polyacrylamide gel electrophoresis (PAGE), to detect the presence of cleaved and uncleaved molecules.

The following is but one example of a method by which suitable target sites can be identified and is not limiting in this invention. Generally, the method involves identifying potential cleavage sites for a hammerhead ribozyme, and then testing each of these sites to determine their suitability as targets by ensuring that secondary structure formation is minimal.

The mRNA sequences are compared in an appropriate target region. Putative ribozyme cleavage sites are found. These sites represent the preferable sites for hammerhead ribozyme cleavage within these target mRNAs.

Short RNA substrates corresponding to each of the mRNA sites are designed. Each substrate is composed of two to three nucleotides at the 5' and 3' ends that will not base pair with a corresponding ribozyme recognition region. The unpaired regions flanked a central region of 12–14 nucleotides to which complementary arms in the ribozyme are designed.

The structure of each substrate sequence is predicted using a PC fold computer program. Sequences which give a positive free energy of binding are accepted. Sequences which give a negative free energy are modified by trimming one or two bases from each of the ends. If the modified sequences are still predicted to have a strong secondary structure, they are rejected.

After substrates are chosen, ribozymes are designed to each of the RNA substrates. Ribozyme folding is also analyzed using PC fold.

Ribozyme molecules are sought which form hammerhead motif stem II (see FIG. 1) regions and contain flanking arms which are devoid of intramolecular base pairing. Often the ribozymes are modified by trimming a base from the ends of the ribozyme, or by introducing additional base pairs in stem II to achieve the desired fold. Ribozymes with incorrect folding are rejected. After substrate/ribozyme pairs are found to contain correct intramolecular structures, the molecules are folded together to predict intermolecular interactions. A schematic representation of a ribozyme with its coordinate base pairing to its cognate target sequence is shown in FIG. 1.

Those targets thought to be useful as ribozyme targets can be tested to determine accessibility to nucleic acid probes in a ribonuclease H assay (see below). This assay provides a quick test of the use of the target site without requiring synthesis of a ribozyme. It can be used to screen for sites most suited for ribozyme attack.

Synthesis of Ribozymes

Ribozymes useful in this invention can be produced by gene transcription as described by Cech, supra, or by chemical synthesis. Chemical synthesis of RNA is similar to that for DNA synthesis. The additional 2'—OH group in RNA, however, requires a different protecting group strategy to deal with selective 3'–5' internucleotide bond formation, and with RNA susceptibility to degradation in the presence of bases. The recently developed method of RNA synthesis utilizing the t-butyldimethylsilyl group for the protection of the 2' hydroxyl is the most reliable method for synthesis of ribozymes. The method reproducibly yields RNA with the correct 3'–5' internucleotide linkages, with average coupling yields in excess of 99%, and requires only a two-step deprotection of the polymer.

A method, based upon H-phosphonate chemistry of phosphoroamidites gives a relatively lower coupling efficiency than a method based upon phosphoroamidite chemistry. This is a problem for synthesis of DNA as well. A promising approach to scale-up of automatic oligonucleotide synthesis has been described recently for the H-phosphonates. A combination of a proper coupling time and additional capping of "failure" sequences gave high yields in the synthesis of oligodeoxynucleotides in scales in the range of 14 μmoles with as little as 2 equivalents of a monomer in the coupling step. Another alternative approach is to use soluble polymeric supports (e.g., polyethylene glycols), instead of the conventional solid supports. This method can yield short oligonucleotides in hundred milligram quantities per batch utilizing about 3 equivalents of a monomer in a coupling step.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Exogenous delivery of ribozymes benefits from chemical modification of the backbone, e.g., by the overall negative charge of the ribozyme molecule being reduced to facilitate diffusion across the cell membrane. The present strategies for reducing the oligonucleotide charge include: modification of internucleotide linkages by methylphosphonates, use of phosphoramidites, linking oligonucleotides to positively charged molecules, and creating complex packages composed of oligonucleotides, lipids and specific receptors or effectors for targeted cells. Examples of such modifications include sulfur-containing ribozymes containing phosphorothioates and phosphorodithioates as internucleotide linkages in RNA. Synthesis of such sulfur-modified ribozymes is achieved by use of the sulfur-transfer reagent, $^3$H-1,2-benzenedithiol-3-one 1,1-dioxide. Ribozymes may also contain ribose modified ribonucleotides. Pyrimidine analogues are prepared from uridine using a procedure employing diethylamino sulphur trifluoride (DAST) as a starting reagent. Ribozymes can also be either electrostatically or covalently attached to polymeric cations for the purpose of reducing charge. The polymer can be attached to the ribozyme by simply converting the 3'-end to a ribonucleoside dialdehyde which is obtained by a periodate cleavage of the terminal 2',3'-cis diol system. Depending on the specific requirements for delivery systems, other possible modifications may include different linker arms containing carboxyl, amino or thiol functionalities. Yet further examples include use of methylphosphonates and 2'-O-methylribose and 5' or 3' capping or blocking with $m_7$GpppG or $m_3^{2,2,7}$GpppG.

For example, a kinased ribozyme is contacted with guanosine triphosphate and guanyltransferase to add an $m^3$G cap to the ribozyme. After such synthesis, the ribozyme can be gel purified using standard procedure. To ensure that the ribozyme has the desired activity, it may be tested with and without the 5' cap using standard procedures to assay both its enzymatic activity and its stability.

Synthetic ribozymes, including those containing various modifiers, can be purified by high pressure liquid chromatography (HPLC). Other liquid chromatography techniques, employing reverse phase columns and anion exchangers on silica and polymeric supports may also be used.

There follows an example of the synthesis of one ribozyme. (See, Dudycz, U.S. patent application Ser. No. 07/884,436, filed May 14, 1992, hereby incorporated by reference herein.) A solid phase phosphoramidite chemistry is employed. Monomers used are 2'-tert-butyl-dimethylsilyl cyanoethylphosphoramidities of uridine, N-benzoyl-cytosine, N-phenoxyacetyl adenosine and guanosine (Glen Research, Sterling, Va.). Solid phase synthesis is carried out on either an ABI 394 or 380B DNA/RNA synthesizer using the standard protocol provided with each machine. The only exception is that the coupling step is increased from 10 to 12 minutes. The phosphoramidite concentration is 0.1M. Synthesis is done on a 1 μmole scale using a 1 μmole RNA reaction column (Glen Research). The average coupling efficiencies are between 97% and 98% for the 394 model, and between 97% and 99% for the 380B model, as determined by a calorimetric measurement of the released trityl cation.

Blocked ribozymes are cleaved from the solid support (e.g., CPG), and the bases and diphosphoester moiety deprotected in a sterile vial by dry ethanolic ammonia (2 mL) at 55° C. for 16 hours. The reaction mixture is cooled on dry ice. Later, the cold liquid is transferred into a sterile screw cap vial and lyophilized.

To remove the 2'-tert-butyl-dimethylsilyl groups from the ribozyme, the residue is suspended in 1M tetra-n-butylammonium fluoride in dry THF (TBAF), using a 20 fold excess of the reagent for every silyl group, for 16 hours at ambient temperature (about 15°–25° C). The reaction is quenched by adding an equal volume of sterile 1M triethylamine acetate, pH 6.5. The sample is cooled and concentrated on a Speed-Vac to half the initial volume.

The ribozymes are purified in two steps by HPLC on a C4 300 Å 5 mm DeltaPak column in an acetonitrile gradient.

The first step, or "trityl on" step, is a separation of 5'-DMT-protected ribozyme(s) from failure sequences lacking a 5'-DMT group. Solvents used for this step are: A (0.1M triethylammonium acetate, pH 6.8) and B (acetonitrile). The elution profile is: 20% B for 10 minutes, followed by a linear gradient of 20% B to 50% B over 50 minutes, 50% B for 10 minutes, a linear gradient of 50% B to 100% B over 10 minutes, and a linear gradient of 100% B to 0% B over 10 minutes.

The second step is a purification of a completely deblocked ribozyme by a treatment of 2% trifluoroacetic acid on a C4 300 Å 5 mm DeltaPak column in an acetonitrile gradient. Solvents used for this second step are: A (0.1M triethylammonium acetate, pH 6.8) and B (80% acetonitrile, 0.1M triethylammonium acetate, pH 6.8). The elution profile is: 5% B for 5 minutes, a linear gradient of 5% B to 15% B over 60 minutes, 15% B for 10 minutes, and a linear gradient of 15% B to 0% B over 10 minutes.

The fraction containing ribozyme is cooled and lyophilized on a SpeedVac. Solid residue is dissolved in a minimum amount of ethanol and sodium perchlorate in acetone. The ribozyme is collected by centrifugation, washed three times with acetone, and lyophilized.

Expression Vector

While synthetic ribozymes are preferred in this invention, those produced by expression vectors can also be used. (See, McSwiggen, U.S. patent application Ser. No. 07/884,431, filed May 14, 1992, hereby incorporated by reference herein.) In designing a suitable ribozyme expression vector the following factors are important to consider. The final ribozyme must be kept as small as possible to minimize unwanted secondary structure within the ribozyme. A promoter (e.g., the human cytomegalovirus immediate early promoter or human beta actin promoter) should be chosen to be a relatively strong promoter, and expressible both in vitro and in vivo (e.g., the human cytomegalovirus immediate early promoter or human beta actin promoter). Such a promoter should express the ribozyme at a level suitable to effect production of enough ribozyme to destroy a target RNA, but not at too high a level to prevent other cellular activities from occurring (unless cell death itself is desired).

A hairpin at the 5' end of the ribozyme is useful to ensure that the required transcription initiation sequence (GG or GGG or GGGAG) does not bind to some other part of the ribozyme and thus affect regulation of the transcription process. The 5' hairpin is also useful to protect the ribozyme from 5'–3' exonucleases. A selected hairpin at the 3' end of the ribozyme gene is useful since it acts as a transcription termination signal, and protects the ribozyme from 3'–5' exonuclease activity. One example of a known termination signal is that present on the T7 RNA polymerase system. This signal is about 30 nucleotides in length. Other 3' hairpins of shorter length can be used to provide good termination and RNA stability. Such hairpins can be inserted within the vector sequences to allow standard ribozymes to be placed in an appropriate orientation and expressed with such sequences attached.

Poly(A) tails are also useful to protect the 3' end of the ribozyme. These can be provided by either including a poly(A) signal site in the expression vector (to signal a cell to add the poly(A) tail in vivo), or by introducing a poly(A) sequence directly into the expression vector. In the first approach the signal must be located to prevent unwanted secondary structure formation with other parts of the ribozyme. In the second approach, the poly(A) stretch may reduce in size over time when expressed in vivo, and thus the vector may need to be checked over time. Care must be taken in addition of a poly(A) tail which binds poly(A) binding proteins which prevent the ribozyme from acting.

Ribozyme Testing

Once the desired ribozymes are selected, synthesized and purified, they are tested in kinetic and other experiments to determine their utility. An example of such a procedure is provided below.

Preparation of Ribozyme

Crude synthetic ribozyme (typically 350 µg at a time) is purified by separation on a 15% denaturing polyacrylamide gel (0.75 mm thick, 40 cm long) and visualized by UV shadowing. Once excised, gel slices containing full length ribozyme are soaked in 5 ml gel elution buffer (0.5M NH$_4$OAc, 1 mM EDTA) overnight with shaking at 4° C. The eluent is desalted over a C-18 matrix (Sep-Pak cartridges, Millipore, Milford, Mass.) and vacuum dried. The dried RNA is resuspended in 50–100 µl TE (TRIS 10 mM, EDTA 1 mM, pH 7.2). An aliquot of this solution is diluted 100-fold into 1 ml TE, half of which is used to spectrophotometrically quantitate the ribozyme solution. The concentration of this dilute stock is typically 150–800 nM. Purity of the ribozyme is confirmed by the presence of a single band on a denaturing polyacrylamide gel.

A ribozyme may advantageously be synthesized in two or more portions. (See, Mamone, U.S. patent application Ser. No. 07/882,689, filed May 11, 1992, hereby incorporated by reference herein.) Each portion of a ribozyme will generally have only limited or no enzymatic activity, and the activity will increase substantially (by at least 5–10 fold) when all portions are ligated (or otherwise juxtaposed) together. A specific example of hammerhead ribozyme synthesis is provided below.

The method involves synthesis of two (or more) shorter "half" ribozymes and ligation of them together using T4 RNA ligase. For example, to make a 34 mer ribozyme, two 17 mers are synthesized, one is phosphorylated, and both are gel purified. These purified 17 mers are then annealed to a DNA splint strand complementary to the two 17 mers. (Such a splint is not always necessary.) This DNA splint has a sequence designed to locate the two 17 mer portions with one end of each adjacent each other. The juxtaposed RNA molecules are then treated with T4 RNA ligase in the presence of ATP. The 34 mer RNA so formed is then HPLC purified.

Preparation of Substrates

Approximately 10–30 pmoles of unpurified substrate is radioactively 5' end-labeled with T4 polynucleotide kinase using 25 pmoles of [$\gamma$-$^{32}$P] ATP. The entire labeling mix is separated on a 20% denaturing polyacrylamide gel and visualized by autoradiography. The full length band is excised and soaked overnight at 4° C. in 100 µl of TE (10 mM Tris-HCl pH 7.6, 0.1 mM EDTA).

Kinetic Reactions

For reactions using short substrates (between 8 and 16 bases) a substrate solution is made 1X in assay buffer (75 mM Tris-HCl, pH 7.6; 0.1 mM EDTA, 10 mM MgCl$_2$) such that the concentration of substrate is less than 1 nM. A ribozyme solution (typically 20 nM) is made 1X in assay buffer and four dilutions are made using 1X assay buffer. Fifteen µl of each ribozyme dilution (i.e., 20, 16, 12, 8 and 4 nM) is placed in a separate tube. These tubes and the substrate tube are pre-incubated at 37° C. for at least five minutes.

The reaction is started by mixing 15 µl of substrate into each ribozyme tube by rapid pipetting (note that final ribozyme concentrations are 10, 8, 6, 4, 2 nM). Five µl aliquots are removed at 15 or 30 second intervals and quenched with 5 µl stop solution (95% formamide, 20 mM EDTA xylene cyanol, and bromphenol blue dyes). Following the final ribozyme time point, an aliquot of the remaining substrate is removed as a zero ribozyme control.

The samples are separated on either 15% or 20% polyacrylamide gels. Each gel is visualized and quantitated with an Ambis beta scanner (Ambis Systems, San Diego, Calif.).

For the most active ribozymes, kinetic analyses are performed in substrate excess to determine $K_m$ and $K_{cat}$ values.

For kinetic reactions with long RNA substrates (greater than 15 bases in length) the substrates are prepared by transcription using T7 RNA polymerase and defined templates containing a T7 promoter, and DNA encoding appropriate nucleotides of the target RNA. The substrate solution is made 1X in assay buffer (75 mM Tris-HCl, pH 7.6; 0.1 mM EDTA; 10 mM MgCl$_2$) and contains 58 nanomolar concentration of the long RNA molecules. The reaction is started by addition of gel purified ribozymes to 1 μM concentration. Aliquots are removed at 20, 40, 60, 80 and 100 minutes, then quenched by the addition of 5 μl stop solution. Cleavage products are separated using denaturing PAGE. The bands are visualized and quantitated with an Ambis beta scanner.

Kinetic Analysis

A simple reaction mechanism for ribozyme-mediated cleavage is:

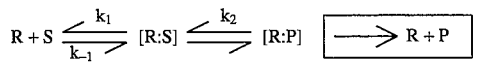

where R=ribozyme, S=substrate, and P=products. The boxed step is important only in substrate excess. Because ribozyme concentration is in excess over substrate concentration, the concentration of the ribozyme-substrate complex ([R:S]) is constant over time except during the very brief time when the complex is being initially formed, i.e.,:

$$\frac{d[R:S]}{dt} = 0$$

where t=time, and thus:

$$(R)(S)k_1 = (RS)(k_2 + k_1).$$

The rate of the reaction is the rate of disappearance of substrate with time:

$$\text{Rate} = \frac{-d(S)}{dt} = k_2(RS)$$

Substituting these expressions:

$$(R)(S)k_1 = 1/k_2 \frac{-d(S)}{dt} (k_2 + k_1)$$

or:

$$\frac{-d(S)}{S} = \frac{k_1 k_2}{(k_2 + k_1)} (R)dt$$

Integrating this expression with respect to time yields:

$$-\ln \frac{S}{S_0} = \frac{k_1 k_2}{(k_2 + k_1)} (R)t$$

where $S_0$=initial substrate. Therefore, a plot of the negative log of fraction substrate uncut versus time (in minutes) yields a straight line with slope:

$$\text{slope} = \frac{k_1 k_2}{(k_2 + k_1)} (R) = k_{obs}$$

where $k_{obs}$=observed rate constant. A plot of slope ($k_{obs}$) versus ribozyme concentration yields a straight line with a slope which is:

$$\text{slope} = \frac{k_1 k_2}{(k_2 + k_1)} \text{ which is } \frac{k_{cat}}{K_m}$$

Using these equations the data obtained from the kinetic experiments provides the necessary information to determine which ribozyme tested is most useful, or active. Such ribozymes can be selected and tested in in vivo or ex vivo systems.

Liposome Preparation

Lipid molecules are dissolved in a volatile organic solvent (CHCl$_3$, methanol, diethylether, ethanol, etc.). The organic solvent is removed by evaporation. The lipid is hydrated into suspension with 0.1× phosphate buffered saline (PBS), then freeze-thawed 3× using liquid nitrogen and incubation at room temperature. The suspension is extruded sequentially through a 0.4 μm, 0.2 μm and 0.1 μm polycarbonate filters at maximum pressure of 800 psi. The ribozyme is mixed with the extruded liposome suspension and lyophilized to dryness. The lipid/ribozyme powder is rehydrated with water to one-tenth the original volume. The suspension is diluted to the minimum volume required for extrusion (0.4 ml for 1.5 ml barrel and 1.5 ml for 10 ml barrel) with 1×PBS and re-extruded through 0.4 μm, 0.2 μm, 0.1 μm polycarbonate filters. The liposome entrapped ribozyme is separated from untrapped ribozyme by gel filtration chromatography (SEPHAROSE CL-4B, BIOGEL A5M). The liposome extractions are pooled and sterilized by filtration through a 0.2 μm filter. The free ribozyme is pooled and recovered by ethanol precipitation. The liposome concentration is determined by incorporation of a radioactive lipid. The ribozyme concentration is determined by labeling with $^{32}$P. Rossi et al., 1992, supra (and references cited therein) describe other methods suitable for preparation of liposomes.

Examples of other useful liposome preparations which display similar degrees of uptake of both a radioactive lipid marker and an entrapped fluorophore by Vero cells showed different fluorescent staining patterns. Specifically, liposomes composed of DPPG/DPPC/Cholesterol (in a ratio of: 50/17/33) gave a punctate pattern of fluorescence, while DOPE/Egg PC/Cholesterol (30/37/33) gave a diffuse, homogeneous pattern of fluorescence in the cytoplasm. Cell fractionation showed that 80% of the entrapped contents from the DPPG/DPPC/Cholesterol formulation was localized in the membrane fraction, whereas the DOPE/Egg PC/Cholesterol formulation was localized in the cytoplasm. Further characterization of the latter formulation showed that after 3 hours, 70% of the fluorescence was cytoplasmic and 30% was in the membrane. After 24 hours, uptake had increased 5 fold and the liposome contents were distributed 50/50 between the cytoplasmic and membrane fractions.

Liposomes containing 15 ribozymes ($^{32}$P-labeled) targeted to the HSV ICP4 mRNA were prepared and incubated with the cells. After 24 hours, 25% of the liposome dose was taken up with approximately 60,000 liposomes per cell. Thirty percent of the delivered ribozyme was intact after 24 hours. Cell fractionation studies showed 40% of the intact ribozyme to be in the membrane fraction and 52% of the intact ribozyme to be in the cytoplasmic fraction.

In Vivo Assay

The efficacy of action of a chosen ribozyme may be tested in vivo using standard procedures in transformed cells or animals which express the target mRNA.

Ribonuclease Protection Assay

The accumulation of target mRNA in cells or the cleavage of the RNA by ribozymes or RNAseH (in vitro or in vivo) can be quantified using an RNAse protection assay. (See, McSwiggen, U.S. patent application Ser. Nos. 07/883,849 and 07/884,073, both filed May 34, 1992, hereby incorporated by reference herein.)

In this method, antisense riboprobes are transcribed from template DNA using T7 RNA polymerase (U.S. Biochemical) in 20 μl reactions containing 1X transcription buffer (supplied by the manufacturer), 0.2 mM ATP, GTP and UTP, 1 U/µl pancreatic RNAse inhibitor (Boehringer Mannheim Biochemicals) and 200 µCi $^{32}$P-labeled CTP (800 Ci/mmol, New England Nuclear) for 1 hour at 37° C. Template DNA is digested with 1 U RNAse-free DNAseI (U.S. Biochemical, Cleveland, Ohio) at 37° C. for 15 minutes and unincorporated nucleotides removed by G-50 SEPHADEX spin chromatography.

In a manner similar to the transcription of antisense probe, the target RNA can be transcribed in vitro using a suitable DNA template. The transcript is purified by standard methods and digested with ribozyme at 37° C. according to methods described later.

Alternatively, afflicted (mRNA-expressing) cells are harvested into 1 ml of PBS, transferred to a 1.5 ml EPPENDORF tube, pelleted for 30 seconds at low speed in a microcentrifuge, and lysed in 70 µl of hybridization buffer (4M guanidine isothiocyanate, 0.1% sarcosyl, 25 mM sodium citrate, pH 7.5). Cell lysate (45 µl) or defined amounts of in vitro transcript (also in hybridization buffer) is then combined with 5 µl of hybridization buffer containing 5×10$^5$ cpm of each antisense riboprobe in 0.5 ml Eppendorf tubes, overlaid with 25 µl mineral oil, and hybridization accomplished by heating overnight at 55° C. The hybridization reactions are diluted into 0.5 ml RNAse solution (20 U/ml RNAseA, 2 U/ml RNAseT1, 10 U/ml RNAse-free DNAseI in 0.4M NaCl), heated for 30 minutes at 37° C., and 10 µl of 20% SDS and 10 µl of Proteinase K (10 mg/ml) added, followed by an additional 30 minutes incubation at 37° C. Hybrids are partially purified by extraction with 0.5 ml of a 1:1 mixture of phenol/chloroform; aqueous phases are combined with 0.5 ml isopropanol, and RNAse-resistant hybrids pelleted for 10 minutes at room temperature (about 20° C.) in a microcentrifuge. Pellets are dissolved in 10 µl loading buffer (95% formamide, 1X TBE, 0.1% bromophenol blue, 0.1% xylene cylanol), heated to 95° C. for five minutes, cooled on ice, and analyzed on 4% polyacrylamide/7M urea gels under denaturing conditions.

Ribozyme Stability

The chosen ribozyme can be tested to determine its stability, and thus its potential utility. Such a test can also be used to determine the effect of various chemical modifications (e.g., addition of a poly(A) tail) on the ribozyme stability and thus aid selection of a more stable ribozyme. For example, a reaction mixture contains 1 to 5 pmoles of 5' (kinased) and/or 3' labeled ribozyme, 15 µg of cytosolic extract and 2.5 mM MgCl$_2$ in a total volume of 100 µl. The reaction is incubated at 37° C. Eight µl aliquots are taken at timed intervals and mixed with 8 µl of a stop mix (20 mM EDTA, 95% formamide). Samples are separated on a 15% acrylamide sequencing gel, exposed to film, and scanned with an Ambis.

A 3'-labeled ribozyme can be formed by incorporation of the $^{32}$P-labeled cordycepin at the 3' OH using poly(A) polymerase. For example, the poly(A) polymerase reaction contains 40 mM Tris, pH 8, 10 mM MgCl$_2$, 250 mM NaCl, 2.5 mM MnCl$_2$; 3 µl $^{32}$P cordycepin, 500 Ci/mM; and 6 units poly(A) polymerase in a total volume of 50 µl. The reaction mixture is incubated for 30 minutes at 37° C.

Effect of Base Substitution Upon Ribozyme Activity

To determine which primary structural characteristics could change ribozyme cleavage of substrate, minor base changes can be made in the substrate cleavage region recognized by a specific ribozyme. For example, the substrate sequences can be changed at the central "C" nucleotide, changing the cleavage site from a GUC to a GUA motif. (See, McSwiggen, U.S. patent application Ser. No. 07/884,074, filed May 14, 1992, hereby incorporated by reference herein.) The $K_{cat}/K_m$ values for cleavage using each substrate are then analyzed to determine if such a change increases ribozyme cleavage rates. Similar experiments can be performed to address the effects of changing bases complementary to the ribozyme binding arms. Changes predicted to maintain strong binding to the complementary substrate are preferred. Minor changes in nucleotide content can alter ribozyme/substrate interactions in ways which are unpredictable based upon binding strength alone. Structures in the catalytic core region of the ribozyme recognize trivial changes in either substrate structure or the three dimensional structure of the ribozyme/substrate complex.

To begin optimizing ribozyme design, the cleavage rates of ribozymes containing varied arm lengths, but targeted to the same length of short RNA substrate can be tested. Minimal arm lengths are required and effective cleavage varies with ribozyme/substrate combinations.

The cleavage activity of selected ribozymes can be assessed using target mRNA substrates. The assays are performed in ribozyme excess and approximate $K_{cat}/K_{min}$ values obtained. Comparison of values obtained with short and long substrates indicates utility in vivo of a ribozyme.

Intracellular Stability of Liposome-delivered Ribozymes

To test the stability of a chosen ribozyme in vivo the following test is useful. Ribozymes are $^{32}$P-end labeled, entrapped in liposomes and delivered to target mRNA-containing cells for three hours. The cells are fractionated and ribozyme is purified by phenol/chloroform extraction. Alternatively, cells (1×10$^7$, T-175 flask) are scraped from the surface of the flask and washed twice with cold PBS. The cells are homogenized by douncing 35 times in 4 ml of TSE (10 mM Tris, pH 7.4, 0.25M Sucrose, mM EDTA). Nuclei are pelleted at 100 xg for 10 minutes. Subcellular organelles (the membrane fraction) are pelleted at 200,000 xg for two hours using an SW60 rotor. The pellet is resuspended in 1 ml of H buffer (0.25M Sucrose, 50 mM HEPES, pH 7.4). The supernatant contains the cytoplasmic fraction (in approximately 3.7 ml). The nuclear pellet is resuspended in 1 ml of 65% sucrose in TM (50 mM Tris, pH 7.4, 2.5 mM MgCl$_2$) and banded on a sucrose step gradient (1 ml nuclei in 65% sucrose TM, 1 ml 60% sucrose TM, 1 ml 55% sucrose TM, 50% sucrose TM, 300 µl 25% sucrose TM) for one hour at 37,000 xg with an SW60 rotor. The nuclear band is harvested and diluted to 10% sucrose with TM buffer. Nuclei are pelleted at 37,000 xg using an SW60 rotor for 15 minutes and the pellet resuspended in 1 ml of TM buffer. Aliquots are size fractionated on denaturing polyacrylamide gels and the intracellular localization determined. By comparison to the migration rate of newly synthesized ribozyme, the various fractions containing intact ribozyme can be determined.

To investigate modifications which would lengthen the half-life of ribozyme molecules intracellularly, the cells may be fractioned as above and the purity of each fraction assessed by assaying enzyme activity known to exist in that fraction.

The various cell fractions are frozen at −70° C. and used to determine relative nuclease resistances of modified ribozyme molecules. Ribozyme molecules may be synthesized with 5 phosphorothioate (ps), or 2'-Omethyl (2'-OMe) modifications at each end of the molecule. These molecules and a phosphodiester version of the ribozyme are end-labeled with $^{32}$P and ATP using T4 polynucleotide kinase. Equal concentrations are added to the cell cytoplasmic extracts and aliquots of each taken at 10 minute intervals. The samples are size fractionated by denaturing PAGE and relative rates of nuclease resistance analyzed by scanning the gel with an Ambis β-scanner. The results show whether the ribozymes are digested by the cytoplasmic extract, and which versions are relatively more nuclease resistant. Modified ribozymes generally maintain 80–90% of the catalytic activity of the native ribozyme when short RNA substrates are employed.

Unlabeled, 5' end-labeled or 3' end-labeled ribozymes can be used in the assays. These experiments can also be performed with human cell extracts to verify the observations.

In one example, Vero or HeLa cells were grown to 90–95% confluency in 175 cm$^2$ tissue culture flasks, scraped into 10 ml of cold phosphate buffered saline (PBS), then washed once in 10 ml of cold PBS and once in 10 ml of cold TSE (10 mM Tris, pH 7.4; 0.25M sucrose; 1 mM EDTA). The cell pellets were resuspended in 4 ml of TSE, dounced 35× on ice, and the released nuclei pelleted by centrifugation at 1000 g for 10 minutes. The nuclear pellet was resuspended in 1 ml of 65% sucrose TM (50 mM Tris, pH 7.4; 2.5 mM MgCl$_2$) and transferred to Beckman ultra-clear tubes. The following sucrose TM solutions were layered on top of the sample: 1 ml 60%, 1 ml 55%, and 25% sucrose to the top of the tube. Gradients were spun in an SW60 rotor at 37,000 g for 1 hour. HeLa nuclei banded at the 55–60% sucrose boundary and Vero nuclei banded at the 50–55% sucrose boundary. Nuclear bands were harvested, diluted to 10% sucrose with TM buffer, and pelleted by centrifugation at 37,000 g for 15 minutes using an SW60 rotor. The nuclear pellet was resuspended in 1 ml of TM buffer. Subcellular organelles and membrane components in the post nuclear supernatant were separated from the cytoplasmic fraction by centrifugation at 200,000 g for 2 hours in an SW60 rotor. The pellet contained the membrane fraction, which was resuspended in 1 ml of H buffer (0.25M sucrose; 50 mM HEPES, pH 7.4), and the supernatant contained the cytoplasmic fraction.

Purity of the various fractions was assessed using enzymatic markers specific for the cytoplasmic and membranous fractions. Three enzyme markers for the membranous fraction were used; hexosaminidase and β-glucocerebrosidase are localized in lysosomes, while alkaline phosphodiesterase is specific to endosomes. Specifically, the assays were as follows:

For N-acetyl-beta-hexosaminidase, the reaction mixture contained 0.3 mg/ml 4-methylumbelliferyl-N-acetylglucosaminide; 20 mM sodium citrate; pH 4.5; 0.01% Triton X-100; and 100 μl of sample in a final volume of 500 μl (Harding et al., 64 *Cell* 393, 1991). The reactions were incubated at 37° C. for 1 hour and stopped by the addition of 1.5 ml of stop buffer (0.13M glycine, 0.07M NaCl, 0.08M sodium carbonate, pH 10.6). The reaction product was quantitated in a Hitachi F-4010 fluorescence spectrophotometer by excitation of the fluorophore at 360 nm and analysis of the emission at 448 nm.

For Alkaline Phosphodiesterase, the assay medium contained 25 mM CAPS (3-(Cyclohexylamino)-propanesulfonic acid), pH 10.6; 0.05% Triton X-100; 15 mM MgCl$_2$; 1.25 mg/ml Thymidine-5'-monophosphate-p-nitrophenyl ester; and 100 μl of sample in a total reaction volume of 200 μl. The reactions were incubated at 37° C. for 2 hours, then diluted to 1 ml with H$_2$O and the absorbance was measured at 400 nm (Razell and Khorana, 234 *J. Biol. Chem.* 739, 1959).

For β-glucocerebrosidase, the reaction contained 85 nM sodium citrate, pH 5.9; 0.12% Triton X-100; 0.1% sodium taurocholate; 5 mM 4-methylumbelliferyl β-D-glucopyranoside; and 125 μl of sample in a total volume of 250 μl (Kennedy and Cooper, 252 *Biochem. J.* 739, 1988). The reaction was incubated at 37° C. for 1 hour and stopped by the addition of 0.75 ml of stop buffer. Product formation was measured in a fluorescence spectrophotometer by using an excitation wavelength of 360 nm and analysis of the emission at 448 nm.

The cytoplasmic enzyme marker, lactate dehydrogenase, was assayed in an assay mixture containing 0.2M Tris; pH 7.4; 0.22 mM NADH; 1 mM sodium pyruvate; and 50 μl of sample in a final volume of 1.05 ml. Enzyme levels were determined by decreased absorbency at 350 nm resulting from the oxidation of NADH at room temperature (Silverstein and Boyer, 239 *J. Biol. Chem.* 3901, 1964).

Lactate dehydrogenase was found predominantly in the cytoplasmic fractions of both Vero and HeLa cells, while β-glucocerebrosidase and alkaline phosphodiesterase were found almost exclusively in the membranous fractions. The hexosaminidase activity in Vero cell fractions was concentrated in the membranous fraction (70%) with about 20% in the cytoplasmic fraction. The isolation of enzyme markers with the appropriate cellular compartment demonstrated that cytoplasmic, membranous and nuclear fractions can be isolated with minimal intercompartmental contamination using this fractionation scheme.

Nuclease Stability of Ribozymes and mRNA

The simplest and most sensitive way to monitor nuclease activity in cell fractions is to use end-labeled oligonucleotides. However, high levels of phosphatase activity in some biological extracts gives ambiguous results in nuclease experiments when $^{32}$P-5'-end-labeled oligonucleotides are used as substrates. To determine the phosphatase activity in the extracts, cellular fractions were incubated with cold ribozymes and trace amounts of 5'-end-labeled ribozyme in the presence of 1 mM Mg$^{+2}$ (or Zn$^{+2}$ with HeLa cytoplasmic extracts) to optimize digestion. After polyacrylamide gel electrophoresis of samples, digestion of the oligonucleotide was assessed both by staining and by autoradiography.

Specifically, the basic oligonucleotide digestion reaction contained substrate nucleic acid (an RNA oligonucleotide of 36 nucleotides) and cell fraction extract in a total volume of 100 μl. Aliquots (7 μl) were taken after various periods of incubation at 37° C. and added to 7 μl of gel loading buffer (95% formamide, 0.1% bromophenol blue, 0.1% xylene cyanol, and 20 mM EDTA). The samples were separated by electrophoresis on a 7M urea, 20% polyacrylamide gel. Intact ribozymes were visualized either by staining with Stains-all (United States Biochemical, Cleveland, Ohio), or autoradiography of labeled ribozyme. The stained gels and X-ray films were scanned on a Bio 5000 density scanner (U.S. Biochemical). Ribozymes were 5' end-labeled with T4 polynucleotide kinase (U.S. Biochemical) using 10 μCi of $^{32}$P γ-ATP (3,000 Ci/mmole, New England Nuclear, Boston, Mass.), and 20–25 pmoles of ribozymes. The unincorporated nucleotides were separated from the product by G-50 spin chromatography. Nuclease assays contained 1–2 pmoles of $^{32}$P-labeled ribozyme. All oligonucteotides were synthesized on an Applied Biosystems 394 DNA/RNA synthesizer (Applied Biosystems Inc., Foster City, Calif.) according to manufacturer's protocols. The nuclear fractions were resuspended in a buffer containing 2.5 mM MgCl$_2$. Experiments involving the nuclear fractions were performed in the presence of 1 mM Mg$^{+2}$, or in combination. with 1 mM Mn$^{+2}$, Ca$^{+2}$, or Zn$^{+2}$.

To measure the stability of mRNA, Vero cells were infected with herpes simplex virus (HSV) at a M.O.I. of 5 and total RNA was extracted (Chomczynski and Sacchi, 162

*Anal. Biochem.* 156, 1987). An RNAse protection assay was used to detect mRNA after incubation of total infected cellular RNA in cytoplasmic extracts. RNA probes were produced from PCR-amplified template DNA using T7 RNA polymerase (U.S. Biochemical) in the presence of $^{32}$P α-CTP (3,000 Ci/mmole, New England Nuclear, Boston, MA). Template DNA was inactivated with 1 unit of RNAse-free DNAseI for 15 minutes at 37° C. Unincorporated nucleotides were removed by G-50 spin chromatography. Samples (6 μl) were taken from the nuclease assays after various periods of incubation at 37° C., added to 40 μl of 4M GUSCN buffer (4M guanidinium thiocyanate; 25 mM sodium citrate, pH 7; 0.5% sarcosyl; and 0.1M 2-mercaptoethanol), and 5 μl of $^{32}$P-labeled RNA probe (5×10$^5$ cpm/5 μl, specific activity of 1.8×10$^6$ cpm/μg) in 4M GUSCN buffer. Hybridization reactions were covered with mineral oil and incubated at 55° C. for 12–16 hours, after which the hybridization reaction was mixed with 500 μl of RNAse buffer (0.4M NaCl, 20 μg/ml RNAseA, 2 units/ml T1 RNAse) and incubated for 30 minutes at 37° C. RNAse activity was quenched by incubation with 10 μl of 20% SDS and 10 μl of proteinase K (20 mg/ml), and the RNA was extracted Using a phenol/chloroform mixture. The protected RNA fragment was purified by precipitation with an equal volume of isopropanol in the presence of 20 μg of carrier yeast tRNA. The RNA pellets were resuspended in gel loading buffer, heated to 95° C. for 5 minutes and separated by electrophoresis on a 5% polyacrylamide, 7M urea gel. Protected fragments were visualized by autoradiography, and the films were scanned with a Bio 5000 density scanner.

In experiments using these methods, the rate of digestion of ribozymes in Vero cell extracts was similar, demonstrating the lack of significant phosphatase activity in Vero cellular fractions. Similar results were observed with HeLa cellular fractions. In most extracts, ladders of digested fragments were observed; such ladders would not be expected if digestion was an artifact of phosphatase action. Thus, digestion using 5' end-labeled ribozymes is an accurate assessment of nuclease action in cellular extracts.

In other experiments, labeled ribozymes were incubated in various Vero and HeLa cellular fractions. Incubation of ribozymes in either membranous or nuclear fractions resulted in a linear decrease of intact molecules over time. In contrast, no digestion of ribozymes occurred during a 24 hour incubation in Vero cytoplasmic extracts, and HeLa cytoplasmic extracts exhibited a 20–30 minute delay in the onset of RNA digestion. After this refractory period, the rate of digestion was linear but not as rapid as the rates observed in any of the nuclear or membranous fractions.

The effect of four divalent cations ($Mg^{+2}$, $Mn^{+2}$, $Ca^{+2}$, and $Zn^{+2}$) on the nuclease activity of the cellular fractions was assessed. Vero cytoplasmic extracts were stimulated by the addition of 1 mM $Mg^{+2}$ or $Mn^{+2}$, while $Ca^{+2}$ or $Zn^{+2}$ had no effect. Nuclease activity in HeLa cytoplasmic extracts was enhanced only by the addition of 1 mM $Zn^{+2}$. Both Vero and HeLa membranous fractions exhibited maximum nuclease activity with the addition of $Mg^{+2}$ or $Mn^{+2}$ ions, while the addition of $Ca^{+2}$ significantly reduced activity of the HeLa membranous fraction and abolished nuclease activity in the Vero membranous fraction. Addition of $Zn^{+2}$ to both membranous fractions resulted in a loss of all RNAse activity. The Vero nuclear extract demonstrated roughly equivalent nuclease activity in the presence of either $Mg^{+2}$ alone or a $Mg^{+2}$ and $Mn^{+2}$ ion combination, less in the presence of $Mg^{+2}$ and $Ca^{+2}$, and no activity in the presence of $Mg^{+2}$ and $Zn^{+2}$. The effects of cation addition were not as dramatic with HeLa nuclear extracts. The nuclease activity of these fractions was greatest in the presence of $Mg^{+2}$ alone or $Mg^{+2}$ and $Ca^{+2}$ and decreased slightly with the addition of $Mn^{+2}$ or $Zn^{+2}$ to the $Mg^{+2}$ present in the extracts.

To verify that nuclease activity was dependent upon added divalent cations, nuclease assays were performed using 1 mM $Mg^{+2}$ in the presence and absence of 20 mM EDTA. For the HeLa cytoplasmic fractions, the $Mg^{+2}$ was replaced with 1 mM $Zn^{+2}$. The presence of 20 mM EDTA completely abolished nuclease activity in the Vero and HeLa cytoplasmic fractions and Vero nuclear fractions. Nuclease activity in the HeLa membranous and nuclear fractions was partially inhibited by the addition of EDTA, while EDTA had no effect on the nuclease activity in the Vero membranous fraction. For comparative purposes, reactions using DNA oligonucleotides were performed using different Vero fractions. All DNAse activity in Vero cytoplasmic, membranous, and nuclear fractions was inhibited by 20 mM EDTA.

The stability of RNA oligonucleotides and HSV-1 mRNA were compared in the presence and absence of activity-enhancing divalent cations (1 mM $Mg^{+2}$, Vero cells; 1 mM $Zn^{+2}$, HeLa cells). Total cellular RNA from HSV-1 infected Vero cells (8 mg) and tracer amounts of $^{32}$P-5'-end-labeled RNA oligonucleotides (1 pmole) were incubated with Vero or HeLa cytoplasmic extracts. In the absence of divalent cations, no substantial decrease of intact ribozymes was detected in assays, although mRNA was digested in both Vero and HeLa cytoplasmic extracts. After addition of divalent cations, digestion of ribozymes occurred in both Vero and HeLa cytoplasmic fractions. The rate of ribozyme digestion in HeLa extracts increased to levels similar to those observed with mRNA, while the rate of mRNA digestion remained greater than the rate of ribozyme digestion in vero cytoplasmic fractions.

Thus, the stability of hammerhead ribozymes were compared in both Vero and HeLa cell cytoplasmic, membranous and nuclear fractions. Vero cytoplasmic and nuclear fractions were found to require $Mg^{+2}$ for optimal nuclease activity, while the membranous fraction was not altered by the addition of divalent cations. HeLa membranous and nuclear fractions were also activated by $Mg^{+2}$, while the cytoplasmic fractions required $Zn^{+2}$ for nuclease activation. Relative stabilities of ribozymes and mRNAs were compared in Vero and HeLa cytoplasmic fractions. In the absence of appropriate divalent cations, little ribozyme digestion was observed in either cytoplasmic preparation while mRNA was rapidly digested. The addition of $Mg^{+2}$ to Vero cytoplasmic extracts and $Zn^{+2}$ to the HeLa cytoplasmic extracts stimulated ribozyme degradation and enhanced mRNA digestion. These data show that the nuclease sensitivity of ribozymes is cell-type specific, varies with the intracellular compartment studied and may not be able to be predicted from studies with mRNA. Notably, however, ribozymes appear stable in such cellular fractions for a period of time potentially sufficient to have a therapeutically useful activity.

Administration of Ribozyme

Selected ribozymes can be administered prophylactically, or to patients having inflammatory conditions, e.g., by exogenous delivery of the ribozyme to a desired tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of ribozymes are also suitable.

The specific delivery route of any selected ribozyme will depend on the use of the ribozyme. Generally, a specific delivery program for each ribozyme will focus on unmodified ribozyme uptake with regard to intracellular localization, followed by demonstration of efficacy. Alternatively, delivery to these same cells in an organ or tissue of an animal can be pursued. Uptake studies will include uptake assays to evaluate cellular ribozyme uptake, regardless of the delivery vehicle or strategy. Such assays will also determine the intracellular localization of the ribozyme following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:

a. encapsulation in liposomes, b. transduction by retroviral vectors, c. conjugation with cholesterol, d. localization to nuclear compartment utilizing nuclear targeting site found on most nuclear proteins, e. neutralization of charge of ribozyme by using nucleotide derivatives, and f. use of blood stem cells to distribute ribozymes throughout the body.

At least three types of delivery strategies are useful in the present invention, including: ribozyme modifications, particle carrier drug delivery vehicles, and retroviral expression vectors. Unmodified ribozymes, like most small molecules, are taken up by cells, albeit slowly. To enhance cellular uptake, the ribozyme may be modified essentially at random, in ways which reduce its charge but maintains specific functional groups. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge allowing free diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell.

A liposome formulation containing phosphatidylethanolomidomethylthiosuccinimide which can deliver oligonucleotides to lymphocytes and macrophages is useful for certain conditions. Furthermore, a 200 nm diameter liposome of this composition was internalized as well as 100 nm diameter liposomes. The 200 nm liposomes exhibit a ten-fold greater packaging capacity than the 100 nm liposomes and can accommodate larger molecules such as a ribozyme expression vector. This ribozyme delivery system prevents mRNA expression in afflicted primary immune cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration.

Liposomes injected intravenously show accumulation in the liver, lung and spleen. The composition and size can be adjusted so that this accumulation represents 30% to 40% of the injected dose. The remaining dose circulates in the blood stream for up to 24 hours.

The chosen method of delivery should result in cytoplasmic accumulation and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, possibly continuously. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogs may require different dosaging. Descriptions of useful systems are provided in the art cited above, all of which is hereby incorporated by reference herein.

Other embodiments are within the following claims.

---

We claim:

1. An enzymatic RNA molecule which specifically cleaves mRNA produced from the gene encoding tumor necrosis factor-α.

2. The enzymatic RNA molecule of claim 1 wherein said enzymatic RNA molecule is in a hammerhead motif.

3. The enzymatic RNA molecule of claim 1, wherein said enzymatic RNA molecule is in a hairpin, hepatitis Delta virus, group 1 intron, or RNAseP RNA motif.

4. The enzymatic RNA molecule of claim 1, wherein said enzymatic RNA molecule comprises between 5 and 23 bases complementary to said mRNA.

5. The enzymatic RNA molecule of claim 1, wherein said enzymatic RNA molecule comprises between 10 and 18 bases complementary to said mRNA.

6. A mammalian cell in vitro including an enzymatic RNA molecule of claim 1.

7. The cell of claim 6, wherein said cell is a human cell.

8. An expression vector including a nucleic acid encoding the enzymatic RNA molecule of claim 1, in a manner which allow expression of that enzymatic RNA molecule within a mammalian cell in vitro.

\* \* \* \* \*

UNITED STATES PATENT AND TRADEMARK OFFICE
CERTIFICATE OF CORRECTION

PATENT NO. : 5,616,490
DATED : April 1, 1997
INVENTOR(S) : Sean M. Sullivan, et al It is certified that error appears in the above-identified patent and that said Letters Patent is hereby corrected as shown below:

Column 7, Line 21: Delete "109" and insert --100--

Column 7, Line 60: After "therapies" insert --(e.g., --

Signed and Sealed this

Thirteenth Day of October 1998

Attest:

BRUCE LEHMAN

*Attesting Officer*

*Commissioner of Patents and Trademarks*

SEQUENCE LISTING ( 1 ) GENERAL INFORMATION:

( i i i ) NUMBER OF SEQUENCES: 54

( 2 ) INFORMATION FOR SEQ ID NO: 1:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) SEQUENCE DESCRIPTION: SEQ ID NO: 1:

CAGCAGAGGA CCAGCUA                    17

( 2 ) INFORMATION FOR SEQ ID NO: 2:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 2:

GCAACUACAG ACCC                       14

( 2 ) INFORMATION FOR SEQ ID NO: 3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 3:

CCCCUGAAAA CAACCCUCAG ACGC          24

( 2 ) INFORMATION FOR SEQ ID NO: 4:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 4:

CACAUCCCCU GACAAGCUGC CAGGCAGG         28

( 2 ) INFORMATION FOR SEQ ID NO: 5:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 5:

CACAUACUGA CCCA         14

( 2 ) INFORMATION FOR SEQ ID NO: 6:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) SEQUENCE DESCRIPTION: SEQ ID NO: 6:

CCUCUCUCCC CUGGAAAGG         19

( 2 ) INFORMATION FOR SEQ ID NO: 7:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( i i ) SEQUENCE DESCRIPTION: SEQ ID NO: 7:

ACACCAUGAG CACUGAAAGC AUGAUCCGGG AC         32

( 2 ) INFORMATION FOR SEQ ID NO: 8:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) SEQUENCE DESCRIPTION: SEQ ID NO: 8:

GCCCAGGGC UCCAGGC         17

( 2 ) INFORMATION FOR SEQ ID NO: 9:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 9:

GGUGCUUGUU CCUCAGCCUC UUC         23

( 2 ) INFORMATION FOR SEQ ID NO: 10:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 10:

CCACCACGCU CUUC                                           1 4

( 2 ) INFORMATION FOR SEQ ID NO: 11:

( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 11:

AAGAGUUCCC CAG                                            1 3

( 2 ) INFORMATION FOR SEQ ID NO: 12:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) SEQUENCE DESCRIPTION: SEQ ID NO: 12:

AGUCAGAUCA UCUUCUCGAA CCCCGAGUGA CAA            3 3

( 2 ) INFORMATION FOR SEQ ID NO: 13:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 13:

UAGCCCAUGU UGUAGCAAAC CCUCAAGCUG AGGG           3 4

( 2 ) INFORMATION FOR SEQ ID NO: 14:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 14:

UACCUCAUCU ACUCC                                          1 5

( 2 ) INFORMATION FOR SEQ ID NO: 15:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 15:

UCAAGGGCCA AGGCUGCCCC UC                                  2 2

( 2 ) INFORMATION FOR SEQ ID NO: 16:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 16:

CACCCAUGUG CUCCUCACCC A          21

( 2 ) INFORMATION FOR SEQ ID NO: 17:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 17:

CGCAUCGCCG UCUCCUACCA GACCAA      26

( 2 ) INFORMATION FOR SEQ ID NO: 18:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i i ) SEQUENCE DESCRIPTION: SEQ ID NO: 18:

GCCAUCAAGA G          11

( 2 ) INFORMATION FOR SEQ ID NO: 19:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO: 19:

CCGACUAUCU CGACUUUGCC      20

( 2 ) INFORMATION FOR SEQ ID NO: 20:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 20:

UCAUUGCCCU GUGAGGAGGA CGAACAUCCA ACCU    34

( 2 ) INFORMATION FOR SEQ ID NO: 21:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION: SEQ ID NO: 21:

CUUAGGGUCG GAACCCAA      18

( 2 ) INFORMATION FOR SEQ ID NO: 22:

( i ) SEQUENCE CHARACTERISTICS:
        ( A ) LENGTH: 18

( B ) TYPE: nucleic acid
( C ) STRANDEDNESS: single
( D ) TOPOLOGY: linear ( i i ) SEQUENCE DESCRIPTION: SEQ ID NO: 22:

AAACCUGGGA UUCAGGAA                     18

( 2 ) INFORMATION FOR SEQ ID NO: 23:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) SEQUENCE DESCRIPTION: SEQ ID NO: 23:

CUGGCAACCA CUAAGAAU                     18

( 2 ) INFORMATION FOR SEQ ID NO: 24:

( i ) SEQUENCE CHARACTERISTICS:
( A ) LENGTH: 15
( B ) TYPE: nucleic acid
( C ) STRANDEDNESS: single
( D ) TOPOLOGY: linear ( i i ) SEQUENCE DESCRIPTION: SEQ ID NO: 24:

UCCAGAACUC ACUGG                        15

( 2 ) INFORMATION FOR SEQ ID NO: 25:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) SEQUENCE DESCRIPTION: SEQ ID NO: 25:

UGGCCAGAAU GCUGCAGGAC UUGAGA            26

( 2 ) INFORMATION FOR SEQ ID NO: 26:

( i ) SEQUENCE CHARACTERISTICS:
( A ) LENGTH: 27
( B ) TYPE: nucleic acid
( C ) STRANDEDNESS: single
( D ) TOPOLOGY: linear ( i i ) SEQUENCE DESCRIPTION: SEQ ID NO: 26:

AGACCUCACC UAGAAAUUGA CACAAGU           27

( 2 ) INFORMATION FOR SEQ ID NO: 27:

( i ) SEQUENCE CHARACTERISTICS:
( A ) LENGTH: 11
( B ) TYPE: nucleic acid
( C ) STRANDEDNESS: single
( D ) TOPOLOGY: linear ( i i ) SEQUENCE DESCRIPTION: SEQ ID NO: 27:

CUUCCUUGAG A                            11

( 2 ) INFORMATION FOR SEQ ID NO: 28:

( i ) SEQUENCE CHARACTERISTICS:
( A ) LENGTH: 22
( B ) TYPE: nucleic acid
( C ) STRANDEDNESS: single ( D ) TOPOLOGY: linear ( i i ) SEQUENCE DESCRIPTION: SEQ ID NO: 28:

UCUAUUUAUG UUUGCACUUG UG 22

( 2 ) INFORMATION FOR SEQ ID NO: 29:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 29:

AUUAUUUAUU AUUUAUUUAU UAUUUAUUUA UUUA 34

( 2 ) INFORMATION FOR SEQ ID NO: 30:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) SEQUENCE DESCRIPTION: SEQ ID NO: 30:

CAGAUGAAUG UAUUUAUUU 19

( 2 ) INFORMATION FOR SEQ ID NO: 31:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) SEQUENCE DESCRIPTION: SEQ ID NO: 31:

ACCGGGGUAU CC 12

( 2 ) INFORMATION FOR SEQ ID NO: 32:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 32:

GACCCAAUGU AGGAGCUGCC UUGGCUCAG 29

( 2 ) INFORMATION FOR SEQ ID NO: 33:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i i ) SEQUENCE DESCRIPTION: SEQ ID NO: 33:

AGCCCCUGG C 11

( 2 ) INFORMATION FOR SEQ ID NO: 34:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 34:

CCUUCUUUUG AUUAUGUUUU UUAAAAUAUU UAUC                34

( 2 ) INFORMATION FOR SEQ ID NO: 35:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 35:

GUCUAAACAA UGCU                14

( 2 ) INFORMATION FOR SEQ ID NO: 36:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 36:

GUCACUCAUU GCUGAG                16

( 2 ) INFORMATION FOR SEQ ID NO: 37:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) SEQUENCE DESCRIPTION: SEQ ID NO: 37:

CUACUAUUCA GU                12

( 2 ) INFORMATION FOR SEQ ID NO: 38:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 38:

GAAAUAAAGU UUGCUU                16

( 2 ) INFORMATION FOR SEQ ID NO: 39:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i i ) SEQUENCE DESCRIPTION: SEQ ID NO: 39:

CUUUGCCAAA GGCAAAC                17

( 2 ) INFORMATION FOR SEQ ID NO: 40:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 40:

CGUUUCAGAG CCAUGAGGAU GC                   22

( 2 ) INFORMATION FOR SEQ ID NO: 41:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 41:

AUUUGAGUUU GCUAGCUCUU GGAGCUG              27

( 2 ) INFORMATION FOR SEQ ID NO: 42:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION: SEQ ID NO: 42:

CCUACGUGUA UGCCAUCC                        18

( 2 ) INFORMATION FOR SEQ ID NO: 43:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 43:

AGACCUUGGC ACUG                            14

( 2 ) INFORMATION FOR SEQ ID NO: 44:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 44:

UACUCAUCGA ACUCUGCUGA UA                   22

( 2 ) INFORMATION FOR SEQ ID NO: 45:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) SEQUENCE DESCRIPTION: SEQ ID NO: 45:

UGUACAUAAA AA                              12

( 2 ) INFORMATION FOR SEQ ID NO: 46:

( i ) SEQUENCE CHARACTERISTICS:
        ( A ) LENGTH: 11
        ( B ) TYPE: nucleic acid
        ( C ) STRANDEDNESS: single
        ( D ) TOPOLOGY: linear ( i i ) SEQUENCE DESCRIPTION: SEQ ID NO: 46:

AAACUGUGCA A                               11

( 2 ) INFORMATION FOR SEQ ID NO: 47:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) SEQUENCE DESCRIPTION: SEQ ID NO: 47:

AAAGACUAUU CAAAAACUUG UCC      2 3

( 2 ) INFORMATION FOR SEQ ID NO: 48:

( i ) SEQUENCE CHARACTERISTICS:
    ( A ) LENGTH: 34
    ( B ) TYPE: nucleic acid
    ( C ) STRANDEDNESS: single
    ( D ) TOPOLOGY: linear ( i i ) SEQUENCE DESCRIPTION: SEQ ID NO: 48:

AGACGGAGAG UAAACCAAUU CCUAGACUAC CUGC      3 4

( 2 ) INFORMATION FOR SEQ ID NO: 49:

( i ) SEQUENCE CHARACTERISTICS:
    ( A ) LENGTH: 12
    ( B ) TYPE: nucleic acid
    ( C ) STRANDEDNESS: single
    ( D ) TOPOLOGY: linear ( i i ) SEQUENCE DESCRIPTION: SEQ ID NO: 49:

AAGAAAGAGU CA      1 2

( 2 ) INFORMATION FOR SEQ ID NO: 50:

( i ) SEQUENCE CHARACTERISTICS:
    ( A ) LENGTH: 15
    ( B ) TYPE: nucleic acid
    ( C ) STRANDEDNESS: single
    ( D ) TOPOLOGY: linear ( i i ) SEQUENCE DESCRIPTION: SEQ ID NO: 50:

ACUUCAGAGG GAAAG      1 5

( 2 ) INFORMATION FOR SEQ ID NO: 51:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) SEQUENCE DESCRIPTION: SEQ ID NO: 51:

AUUUCAGGCA UACUGACACU UUGCCAGAAA GCA      3 3

( 2 ) INFORMATION FOR SEQ ID NO: 52:

( i ) SEQUENCE CHARACTERISTICS:
    ( A ) LENGTH: 12
    ( B ) TYPE: nucleic acid
    ( C ) STRANDEDNESS: single
    ( D ) TOPOLOGY: linear ( i i ) SEQUENCE DESCRIPTION: SEQ ID NO: 52:

AUAUCAGAAU CA      1 2

( 2 ) INFORMATION FOR SEQ ID NO: 53:

(i) SEQUENCE CHARACTERISTICS:
    (A) LENGTH: 29
    (B) TYPE: nucleic acid
    (C) STRANDEDNESS: single
    (D) TOPOLOGY: linear (ii) SEQUENCE DESCRIPTION: SEQ ID NO: 53:

CAAAAUUGAU AUACUUUUUU CUUAUUUAA      29

(2) INFORMATION FOR SEQ ID NO: 54:

(i) SEQUENCE CHARACTERISTICS:
        (A) LENGTH: 18
        (B) TYPE: nucleic acid
        (C) STRANDEDNESS: single
        (D) TOPOLOGY: linear (ii) SEQUENCE DESCRIPTION: SEQ ID NO: 54:

GAAAUGGUUA AGAAUUUG      18